US011992669B2

United States Patent
Hirschmann et al.

(10) Patent No.: US 11,992,669 B2
(45) Date of Patent: May 28, 2024

(54) SYSTEMS AND METHODS RELATED TO SYRINGES

(71) Applicant: Plas-Tech Engineering, Inc., Lake Geneva, WI (US)

(72) Inventors: Aaron Hirschmann, Lake Geneva, WI (US); Robert Fesus, Lake Geneva, WI (US)

(*) Notice: Subject to any disclaimer, the term of this patent is extended or adjusted under 35 U.S.C. 154(b) by 595 days.

(21) Appl. No.: 16/687,664

(22) Filed: Nov. 18, 2019

(65) Prior Publication Data

US 2020/0155771 A1 May 21, 2020

Related U.S. Application Data

(60) Provisional application No. 62/768,230, filed on Nov. 16, 2018.

(51) Int. Cl.
*A61M 5/50* (2006.01)
*A61M 5/31* (2006.01)

(52) U.S. Cl.
CPC ............ *A61M 5/50* (2013.01); *A61M 5/3134* (2013.01); *A61M 5/3137* (2013.01); *A61M 5/3148* (2013.01)

(58) Field of Classification Search
CPC .... A61M 5/50; A61M 5/5066; A61M 5/3134; A61M 5/3137; A61M 5/3148
See application file for complete search history.

(56) References Cited

U.S. PATENT DOCUMENTS

| 4,391,272 | A | * | 7/1983 | Staempfli | ............ | A61M 5/5013 |
| | | | | | | 604/110 |
| 4,863,427 | A | * | 9/1989 | Cocchi | .................. | A61M 5/508 |
| | | | | | | 604/218 |
| 4,915,692 | A | * | 4/1990 | Verlier | ................ | A61M 5/5013 |
| | | | | | | 604/218 |
| 4,923,443 | A | * | 5/1990 | Greenwood | ........ | A61M 5/5066 |
| | | | | | | 604/110 |
| 4,950,240 | A | * | 8/1990 | Greenwood | ........ | A61M 5/5066 |
| | | | | | | 604/110 |

(Continued)

FOREIGN PATENT DOCUMENTS

| FR | 2791264 | B1 | | 9/2014 | | |
| GB | 2117644 | A | * | 10/1983 | ............. | A61M 5/50 |

(Continued)

OTHER PUBLICATIONS

International Search Report and Written Opinion of the ISA for related application (PCT/US19/62078), dated Feb. 6, 2020, 10 pages.

(Continued)

*Primary Examiner* — Nathan R Price
*Assistant Examiner* — Mark A Igel
(74) *Attorney, Agent, or Firm* — Smith Keane LLP

(57) ABSTRACT

An improved system and method for a syringe capable of reducing re-usage and limiting wasted contents. The syringe has a plunger with a plunger plug that extends beyond the barrel of the syringe when the contents are fully dispensed and prevents the plunger from being drawn backward. The plunger may also consist of a two-piece design that separates upon exceeding a predetermined force when attempting to draw the plunger backward after use.

4 Claims, 9 Drawing Sheets

(56) References Cited

U.S. PATENT DOCUMENTS

| | | | | |
|---|---|---|---|---|
| 4,973,308 A * | 11/1990 | Borras | A61M 5/5066 | 604/110 |
| 4,973,309 A * | 11/1990 | Sultan | A61M 5/5066 | 604/110 |
| 4,990,141 A * | 2/1991 | Byrne | A61M 5/3243 | 604/232 |
| 5,000,735 A * | 3/1991 | Whelan | A61M 5/5066 | 604/110 |
| 5,037,393 A * | 8/1991 | Ellgass | A61M 5/348 | 604/218 |
| 5,085,638 A * | 2/1992 | Farbstein | A61M 5/50 | 604/218 |
| 5,106,372 A * | 4/1992 | Ranford | A61M 5/5013 | 604/218 |
| 5,163,907 A | 11/1992 | Szuszkiewicz | | |
| 5,215,524 A * | 6/1993 | Vallelunga | A61M 5/5066 | 604/218 |
| 5,226,884 A * | 7/1993 | Murphy | A61M 5/5066 | 604/218 |
| 5,304,138 A | 4/1994 | Mercado | | |
| 5,352,203 A * | 10/1994 | Vallelunga | A61M 5/5066 | 604/218 |
| 5,643,211 A * | 7/1997 | Sadowski | A61M 5/30 | 604/218 |
| 5,738,655 A * | 4/1998 | Vallelunga | A61M 5/5066 | 604/218 |
| 5,769,822 A * | 6/1998 | McGary | A61M 5/5066 | 604/110 |
| 5,814,017 A * | 9/1998 | Kashmer | A61M 5/5013 | 604/110 |
| 5,875,976 A * | 3/1999 | Nelson | A61M 5/30 | 285/391 |
| 6,217,550 B1 * | 4/2001 | Capes | A61M 5/348 | 604/218 |
| 6,267,749 B1 * | 7/2001 | Miklos | A61M 5/5013 | 604/218 |
| 6,565,529 B1 * | 5/2003 | Kimber | A61M 5/315 | 604/110 |
| 7,918,821 B2 * | 4/2011 | Mahurkar | A61M 5/3234 | 604/11 |
| 8,361,018 B2 * | 1/2013 | Caizza | A61M 5/50 | 604/110 |
| 8,920,371 B2 | 12/2014 | Caizza et al. | | |
| 9,662,460 B2 * | 5/2017 | Menassa | A61M 5/504 | |
| 2004/0059300 A1 * | 3/2004 | Kosinski | A61M 5/5013 | 604/213 |
| 2008/0065027 A1 | 3/2008 | Sharp | | |
| 2010/0034705 A1 * | 2/2010 | Mundt | A61M 5/14216 | 422/400 |
| 2011/0230844 A1 | 9/2011 | Shaw et al. | | |
| 2012/0165754 A1 | 6/2012 | Chattaraj et al. | | |
| 2012/0289899 A1 * | 11/2012 | Wu | A61M 5/5066 | 604/110 |
| 2013/0030364 A1 | 1/2013 | Wu | | |
| 2013/0079715 A1 | 3/2013 | Wu | | |
| 2013/0079714 A1 | 4/2013 | Wu | | |
| 2017/0239425 A1 * | 8/2017 | Castanon | A61M 5/3293 | |
| 2017/0281853 A1 | 10/2017 | Luo et al. | | |

FOREIGN PATENT DOCUMENTS

| | | | |
|---|---|---|---|
| WO | WO-8401510 A1 * | 4/1984 | |
| WO | 95/27524 A1 | 10/1995 | |
| WO | 98/57687 A1 | 12/1998 | |
| WO | 00/38769 | 7/2000 | |
| WO | 2004033007 A1 | 4/2004 | |
| WO | WO-2004033007 A1 * | 4/2004 | A61M 5/31511 |
| WO | 2013/061290 | 5/2013 | |
| WO | WO-2013061290 A1 * | 5/2013 | A61M 37/0015 |
| WO | 2018/130629 | 7/2018 | |
| WO | WO-2018130629 A1 * | 7/2018 | |

OTHER PUBLICATIONS

EPO, Search Report for related EP Application No. 19883670.2, dated Oct. 20, 2022, 12 pages.

\* cited by examiner

SYSTEMS AND METHODS RELATED TO SYRINGES

RELATED APPLICATIONS

This application claims the benefit of co-pending U.S. Provisional Patent Application Ser. No. 62/768,230, filed 16 Nov. 2018, and entitled "Systems and Methods Related to Syringes," which is incorporated herein by reference in its entirety.

BACKGROUND

Embodiments according to the present invention relate generally to syringes. More specifically, the invention relates to zero hold-up (or substantially complete ejection) and/or one-time use syringes. Syringes typically comprise a barrel and a plunger, whereby the plunger is movable within the barrel to dispense the fluid within the barrel through an outlet or hub connected which may be connected to an output device (e.g., a needle). The syringe is capable of being used repeatedly by drawing fluid back into the barrel by inserting the output device in the desired fluid and drawing the plunger in the reverse direction. Unfortunately, the re-use of syringes is a health concern relating to the communication of disease and other misuse. Therefore, the field of syringes is in need of a syringe that is designed to reduce re-usage.

Embodiments according to the present invention relate also to syringes adapted to make more complete use of the contents of the syringe, such as a medicament.

SUMMARY OF THE INVENTION

The present invention relates to improved systems and methods for a syringe capable of reducing re-usage. More specifically, the present invention is directed to a one-use syringe with a near-zero or zero dead volume. Zero dead volume syringes let you remove all the fluid from the syringe for zero test article loss when dosing and zero fluid loss when sampling.

According to an aspect of an embodiment of a syringe according to the present invention, the syringe includes a barrel extending from an open proximal end to an open distal end. The barrel includes a through-bore extending inward from the open proximal end and a channel extending inward from the open distal end. The through-bore and channel are in fluid communication, wherein the through-bore comprises a through-bore diameter and the channel comprises a channel diameter that is smaller than the through-bore diameter along a channel length. A plunger is slidably received within the barrel through the open proximal end, the plunger comprising a distal end portion disposed at least partially within the through-bore, and longitudinally moveable in an ejection (or distal) direction towards the channel. A snorkel extends from and is supported by the plunger distal end portion, the snorkel having a snorkel length that is greater than the channel length.

According to another embodiment of a syringe according to the present invention, the snorkel may extend from the plunger distal end portion and terminates in a closed free end including a plunger plug, the plunger plug having a major diameter that is greater than the channel diameter. The plunger plug may include at least one slot formed therethrough through an edge thereof, such as a slot that is formed at least substantially parallel to the ejection direction.

According to still another aspect of an embodiment of a syringe according to the present invention, the plunger may further include at least one fin circumferentially engaging the barrel. The at least one fin may include three fins circumferentially engaging the barrel.

According to a further aspect of an embodiment of a syringe according to the present invention, a plunger may be slidably received within the barrel through the open proximal end, the plunger comprising a pushrod coupled to a tip portion through a mating engagement, which may be a bulbous portion received within a catch. The tip portion may be disposed at least partially within the through-bore and in physical, frictional contact with the barrel, and longitudinally moveable in an ejection (e.g., distal) direction towards the channel from the open proximal end. Fictional forces between the tip portion and the barrel in the ejection direction may preferably be greater than a coupling force at the mating engagement, such that when the pushrod is moved in a direction opposite the ejection direction, the mating engagement will break before the tip portion is moved in the direction opposite the ejection direction.

According to a still further aspect of an embodiment of a syringe according to the present invention, a carriage may disposed about and releasably engaged with the tip portion, wherein a force of engagement between the carriage and the tip portion maintains the carriage in a stationary position with respect to the tip portion as the pushrod is moved in a distal direction. Further, the carriage may circumferentially physically (e.g., frictionally) contacts the barrel, and longitudinally contacts an end of the through-bore and additional pressure applied to the proximal end of the pushrod in the distal direction overcomes the force of engagement to allow the carriage to slide along the tip portion as the tip portion continues to move in the distal direction.

DETAILED DESCRIPTION

Although the disclosure hereof enables those skilled in the art to practice the invention, the embodiments described merely exemplify the invention which may be embodied in other ways. While the preferred embodiment has been described, the details may be changed without departing from the invention, which is defined by the claims. It should be noted that like part numbers represent like parts among the various embodiments.

Figure 1:
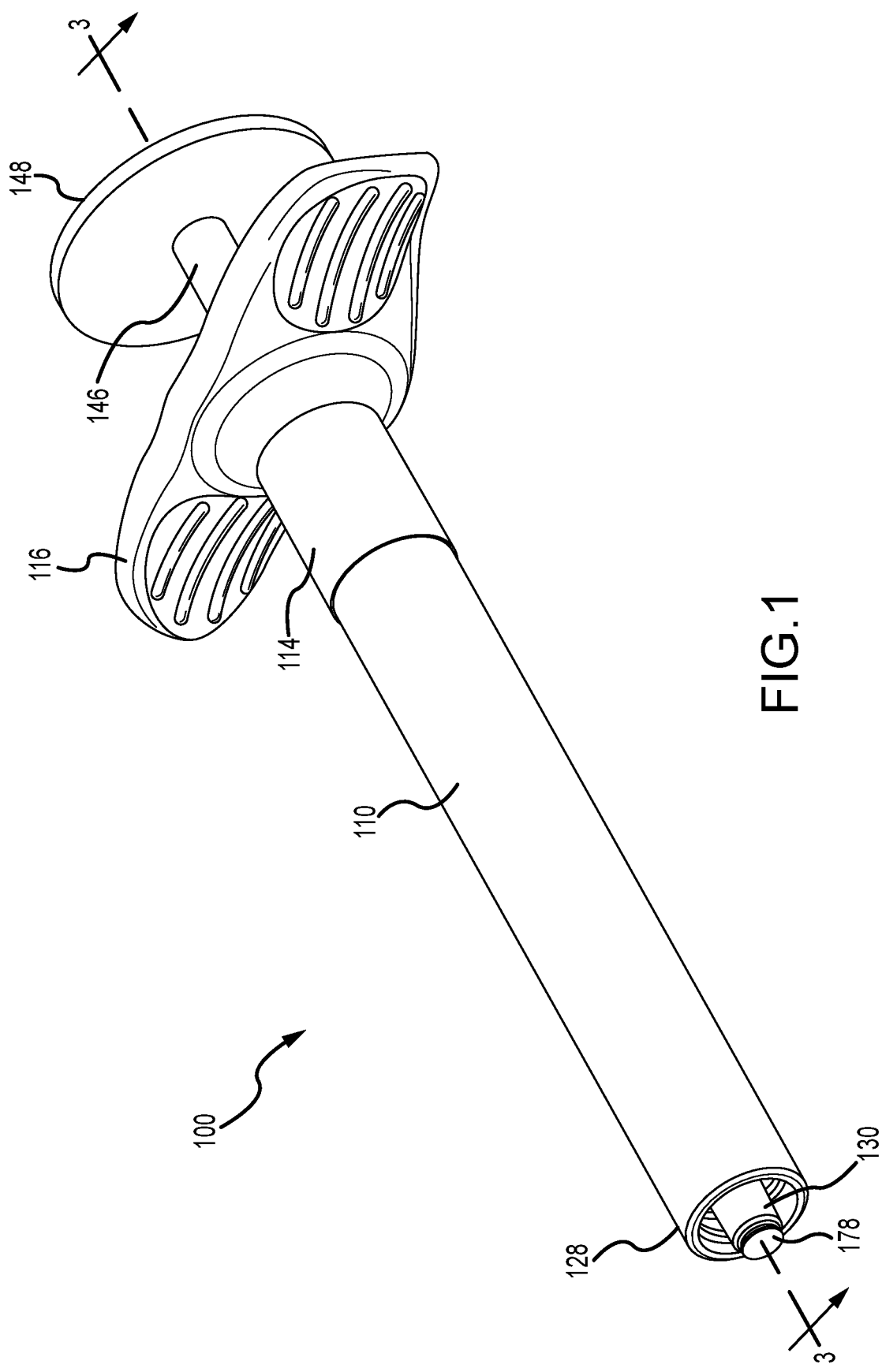
FIG. 1 is a perspective view of a first embodiment of a syringe according to the present invention.
Figure 2:
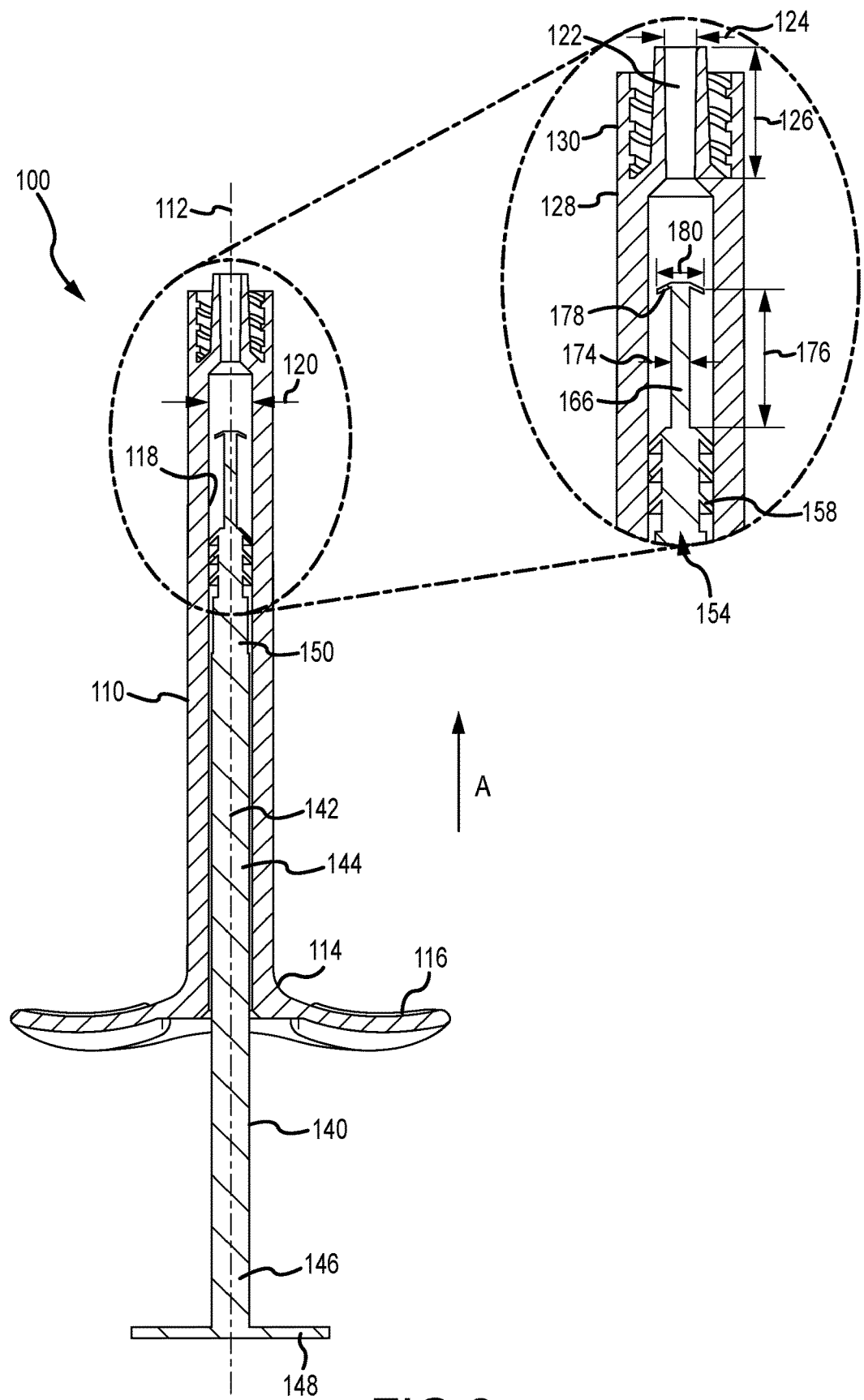
FIG. 2 is a cross-sectional view of the syringe shown in FIG. 1 in a first position.
Figure 3:
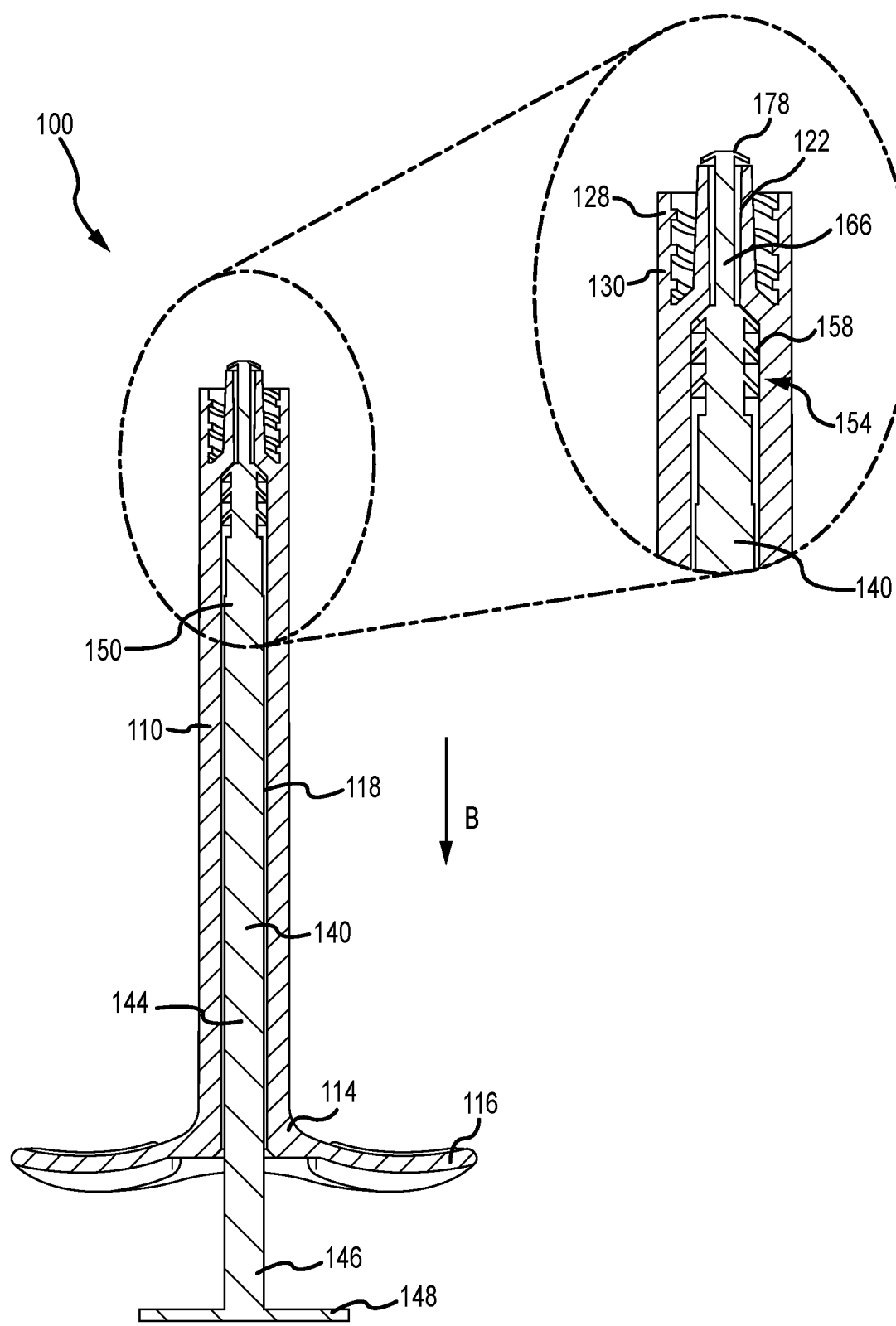
FIG. 3 is a cross-sectional view of the syringe shown in FIG. 1 along line 3-3.

FIGS. 1-3 provide various views of a first exemplary embodiment 100 of a syringe according to the present invention. The syringe 100 preferably comprises a barrel 110 and a plunger 140 receivable and slidable within the barrel 110.

The barrel 110 preferably extends along a barrel axis 112 and comprises a first end portion 114, a through-bore 118, and a second end portion 128. The through-bore 118 preferably extends coaxially with the barrel axis 112 from the first end portion 114 through the second end portion 128 and has a through-bore diameter 120. Preferably located at the first end portion 114 is a member configured to engage with a user's fingers during use, here shown as handles 116, however, other configurations are contemplated. The second end portion 128 preferably comprises a hub 130 configured to receive a needle (not shown) or other dispensing mechanism, for example a Luer-Lok® connection fitting (not shown). The through-bore 118 at the second end portion 128 comprises a channel 122 having a channel diameter 124 and a channel length 126.

The plunger 140 preferably extends along a plunger axis 142 and comprises a pushrod 144 and a tip portion 154 and is preferably made from a thermoplastic elastomer or the like. The pushrod 144 preferably has a first end portion 146 and a second end portion 150. The first end portion 146 preferably has an element configured to be engaged by a user (not shown) during use of the syringe 100, here shown as an end plate 148, but other configurations are contemplated.

The tip portion 154 is preferably contiguous with the second end portion 150 of the pushrod 144 and comprises at least one fin 158 preferably sized and configured to circumferentially engage with the through-bore 118 as the plunger 140 moves therethrough. The tip portion 154 also preferably comprises a solid (or at least having a closed distal end) snorkel 166 with a snorkel diameter 174 and a snorkel length 176 extending along the plunger axis 142 in a direction opposite the end plate 148 and terminating in a plunger plug 178 having a major diameter 180.

The plunger 140 is configured to be received within the barrel 110 whereby the plunger axis 142 is substantially coaxial with the barrel axis 112.

The major diameter 180 of the plunger plug 178 is preferably larger than the snorkel diameter 174 and the channel diameter 124. The snorkel length 176 is preferably longer than the channel length 126. Thereby, when the syringe 100 is being used, the tip portion 154 of the plunger 140 moves within the barrel 110, expelling contents (not shown) through the channel 122 as it moves from approximately the first end portion 114 of the barrel 110 through the second end portion 128 of the barrel 110, shown as direction A.

The snorkel 166 is preferably configured to enter the channel 122 with the plunger plug 178 exiting the channel 122. Because the major diameter 180 of the plunger plug 178 is greater than the channel diameter 124, attempted movement of the plunger in direction B is inhibited by the plunger plug 178 abutting the hub 130.

Figure 4:
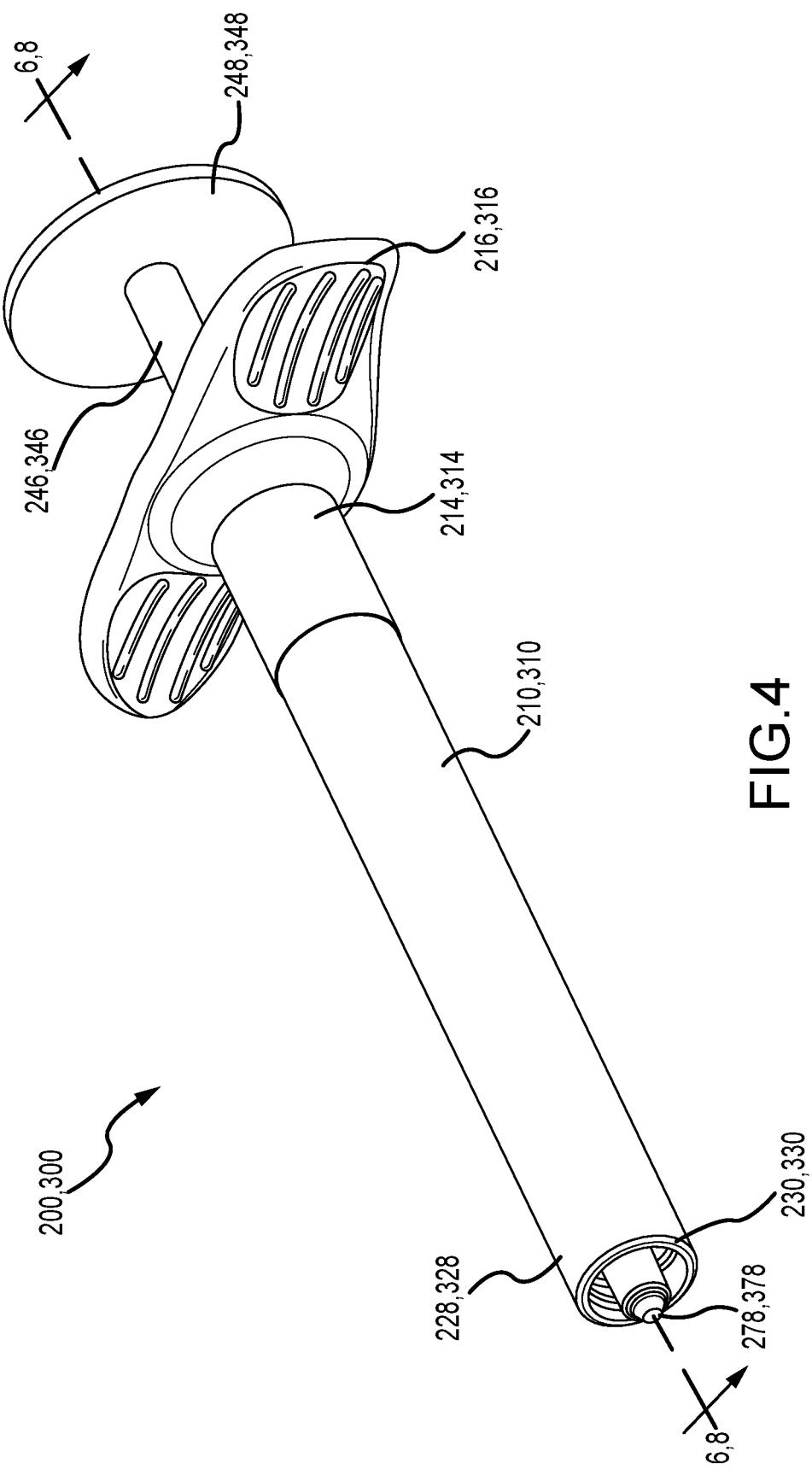
FIG. 4 is a perspective view of a second embodiment and a third embodiment of a syringe according to the present invention.
Figure 5:
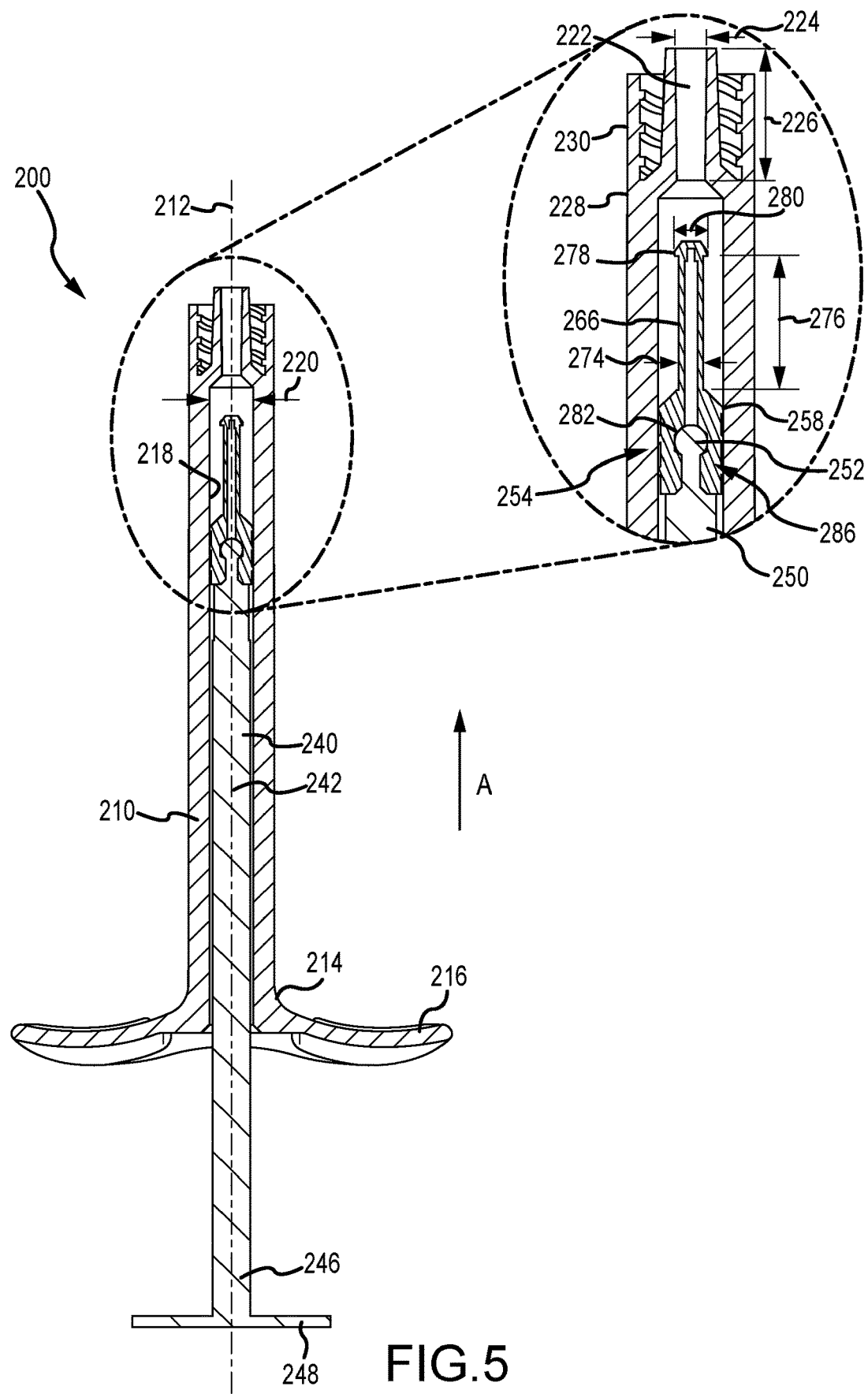
FIG. 5 is a cross-sectional view of the syringe shown in FIG. 4 in a first position.
Figure 6:
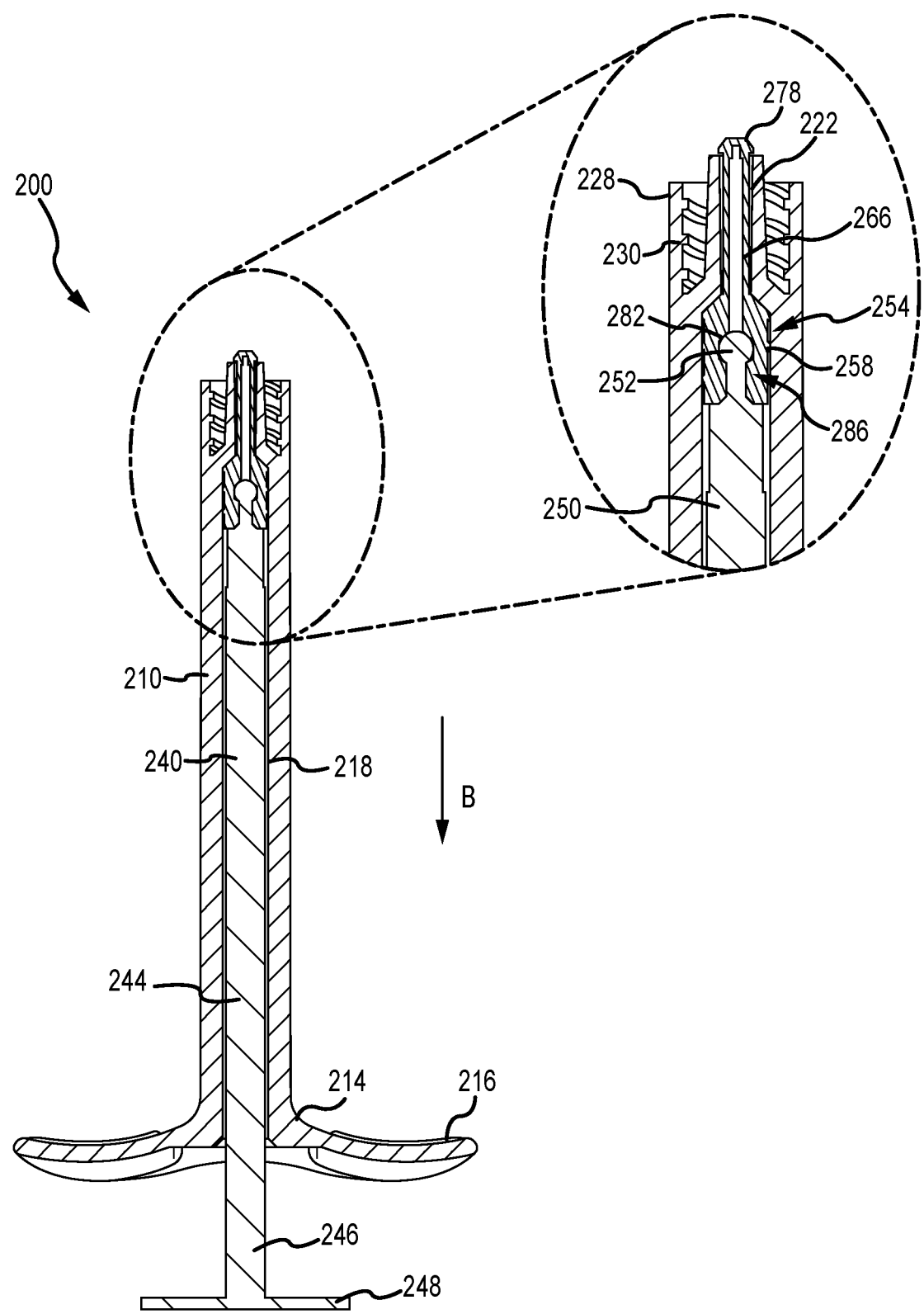
FIG. 6 is a cross-sectional view of the syringe shown in FIG. 4 long line 6-6.

A second exemplary embodiment 200 of a syringe according to the present invention is shown in FIGS. 4-6. Similar to the first embodiment syringe 100 described above, the syringe 200 preferably comprises a barrel 210 and a plunger 240 receivable within the barrel 210.

The barrel 210 is similar in all respects to the first embodiment barrel 110 and therefore a detailed description will be foregone in the interest of clarity and brevity. It should be noted that like part numbers represent like parts among the various embodiments.

The plunger 240 preferably extends along a plunger axis 242 and comprises a pushrod 244 and a tip portion 254. The pushrod 244 preferably has a first end portion 246 and a second end portion 250. The first end portion 246 preferably has an element configured to be engaged by a user during use of the syringe 200, here shown as an end plate 248, but other configurations are contemplated. The second end portion 250 preferably has a bulbous member 252.

The tip portion 254 comprises at least one fin 258 and a catch 282 and is preferably made from a thermoplastic elastomer or the like. The at least one fin 258 is preferably sized and configured to circumferentially engage with the through-bore 218 as the plunger 240 moves therethrough. The tip portion 254 also preferably comprises a snorkel 266 with a snorkel diameter 274 and a snorkel length 276 extending along the plunger axis 242 in a direction opposite the end plate 248 and terminating in a plunger plug 278 having a major diameter 280.

As shown in FIGS. 5 and 6, the bulbous member 252 of the second end portion 250 of the pushrod 244 is preferably configured to be releasably received within the catch 282 of the tip portion 254 to form an axial-tension limiting joint 286. The bulbous member 252 and catch 282 may be provided on opposing respective members (bulb 252 on tip 254 and catch 282 on pushrod) to provide such axial tension limitation.

The plunger 240 is configured to be received within the barrel 210 whereby the plunger axis 242 is substantially coaxial with the barrel axis 212. The major diameter 280 of the plunger plug 278 is preferably larger than the snorkel diameter 274 and the channel diameter 224.

The snorkel length 276 is preferably longer than the channel length 226. Thereby, when the syringe 210 is being used, the tip portion 254 of the plunger 240 moves within the barrel 210, expelling contents (not shown) through the channel 222 as it moves from approximately the first end portion 214 of the barrel 210 through the second end portion 228 of the barrel 210, shown as direction A. The snorkel 266 is configured to enter the channel 222 with the plunger plug 278 exiting the channel 222. Because the major diameter 280 of the plunger plug 278 is greater than the channel diameter 224, movement of the plunger 240 in direction B results in the second end portion 250 of the pushrod 244 separating from the catch 282 in the tip portion 254 because the contact of the plunger plug 278 abutting the hub 230 inhibits movement of the tip portion 254.

That is, the force required to separate the axial-tension limiting joint 286 is less than the force required to cause the plunger plug 278 to reenter the channel 222 in direction B.

Figure 7:
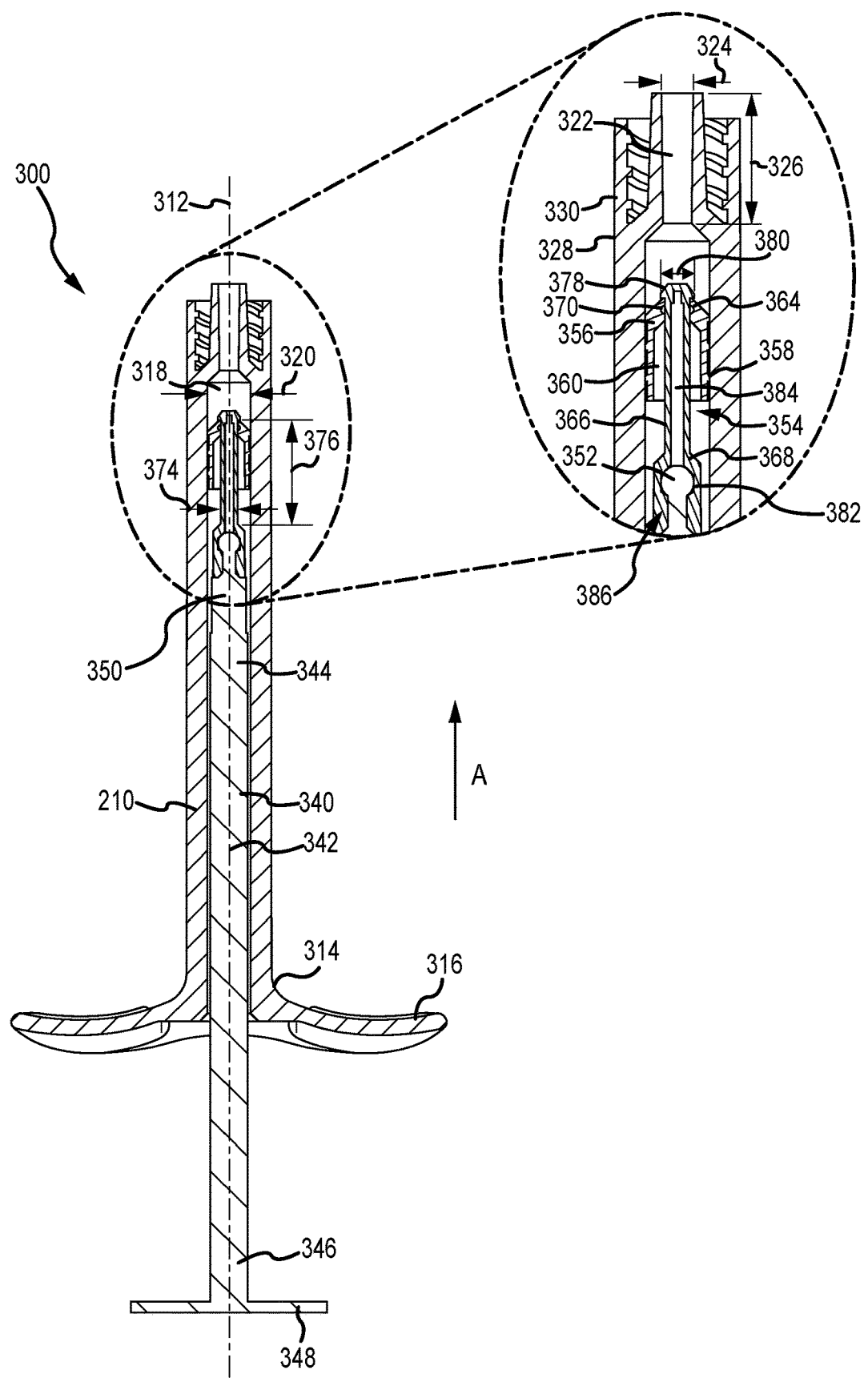
FIG. 7 is a cross-sectional view of a third embodiment syringe in a first position according to the present invention.
Figure 8:
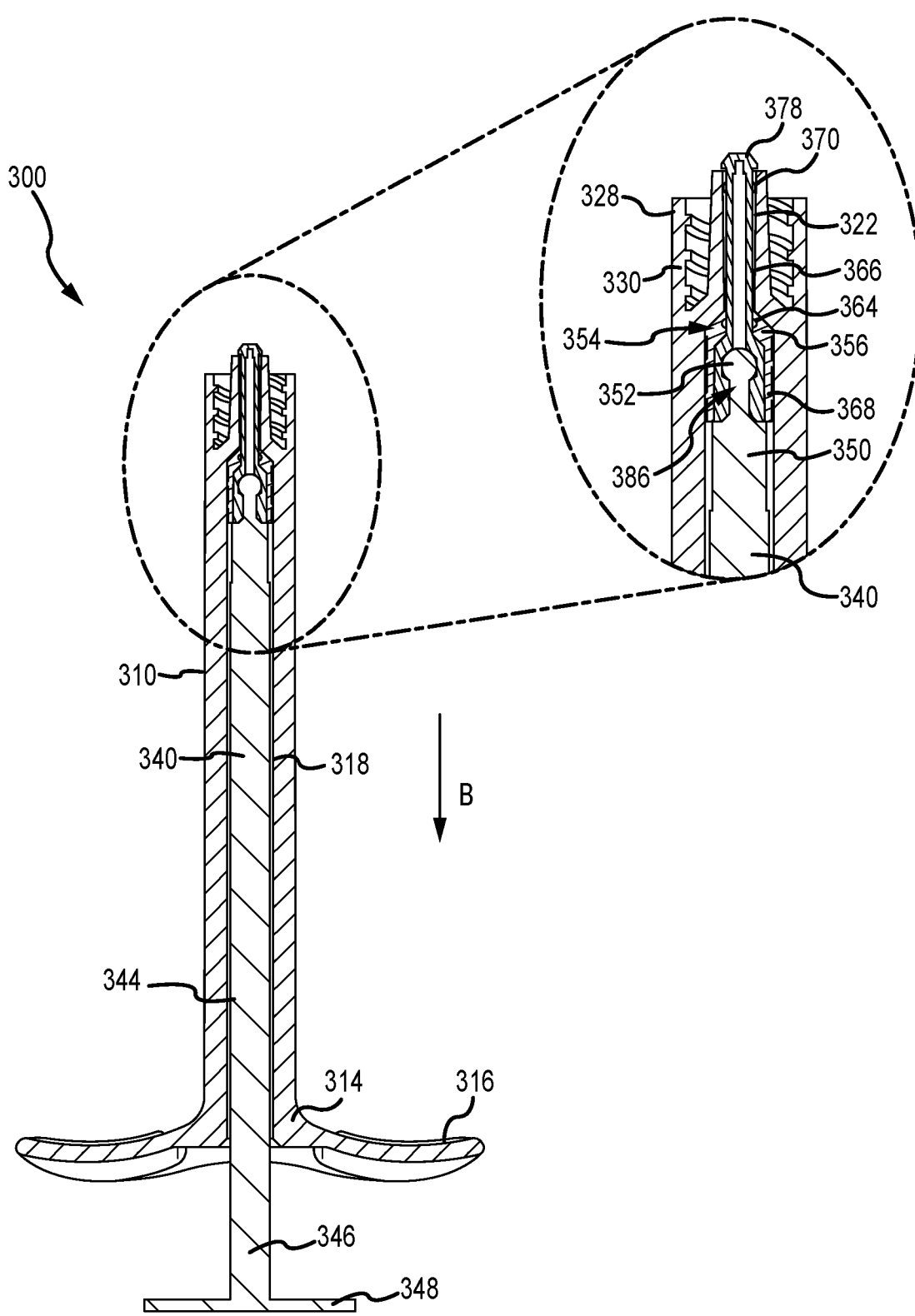
FIG. 8 is a cross-sectional view of the third embodiment syringe in a second position.
Figure 9:
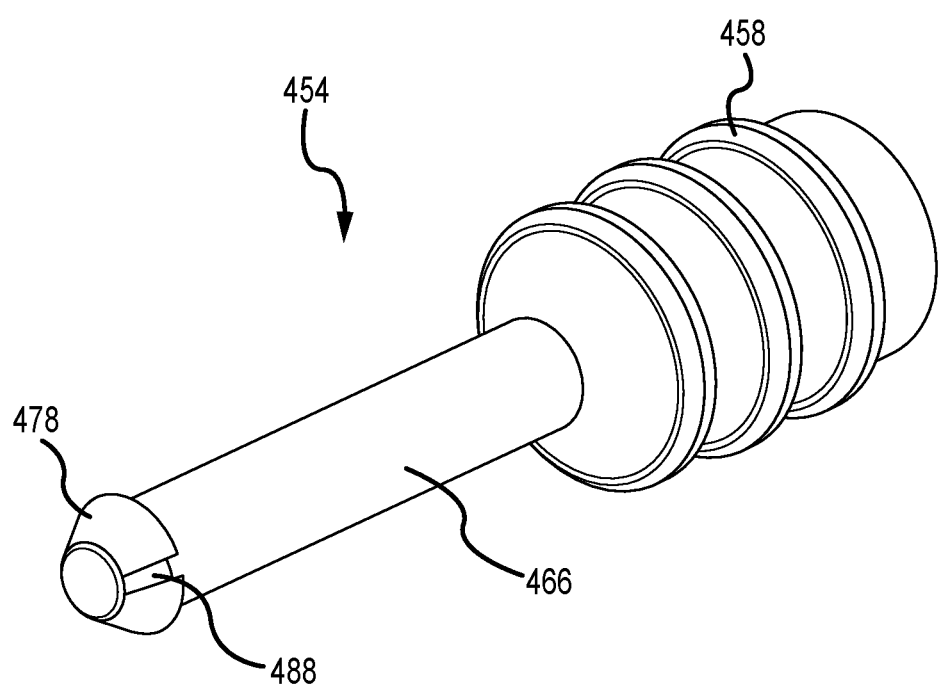
FIG. 9 is a perspective view of a fourth embodiment of a tip portion of a plunger according to the present invention.

FIGS. 4, 7, and 8 show an exemplary third embodiment 300 of a syringe according to the present invention. The syringe 300 preferably comprises a barrel 310 and a plunger 340 receivable within the barrel 310. The barrel 310 is similar in all respects to the first and second embodiment barrels 110,210 and therefore a detailed description will be foregone in the interest of clarity and brevity. As stated above, like part numbers represent like parts among the various embodiments.

The plunger 340 preferably extends along a plunger axis 342 and comprises a pushrod 344 and a tip portion 354. The pushrod 344 preferably has a first end portion 346 and a second end portion 350. The first end portion 346 preferably has an element configured to be engaged by a user during use of the syringe 300, here shown as an end plate 348, but other configurations are contemplated. The second end portion 350 preferably has a bulbous member 352.

The tip portion 354 preferably comprises a carriage 356 and a snorkel 366 and is preferably made from a thermoplastic elastomer or the like. The carriage 356 preferably has at least one fin 358, a cavity 360, and a passage 362 with at least one detent pocket 364. The at least one fin 358 is preferably sized and configured to circumferentially engage with the through-bore 318 of the barrel 310 as the plunger 340 moves therethrough.

The snorkel 366 preferably comprises a base 368 with a catch 382, at least one detent 370, a snorkel diameter 374, a snorkel length 376 extending along the plunger axis 342 in a direction opposite the base 368, a plunger plug 378 having a major diameter 380, and a bore 384 extending along the plunger axis 342 from the base 368 to the plunger plug 378.

The snorkel 366 is preferably configured to transition from a first position (FIG. 7) to a second position (FIG. 8). In the first position, the at least one detent 370 of the snorkel 366 is located within the at least one detent pocket 364 of the carriage 356 and the base 368 is spaced apart from the cavity 360. In the second position, the at least one detent 370 is spaced apart from the at least one detent pocket 364 and the carriage 356 is within the cavity 360.

Preferably, when the syringe 300 is being used, the tip portion 354 of the plunger 340 moves within the barrel 310, with the snorkel 366 in the first position, expelling contents (not shown) through the channel 322 as it moves from approximately the first end portion 314 of the barrel 310 through the second end portion 328 of the barrel 310, shown as direction A. When the carriage 356 meets the hub 330 of the second end portion 328, the carriage 356 is prevented from moving further. Additional force applied to the pushrod 344 at least partially collapses the bore 384 at the location of the at least one detent 370 and allows the at least one detent 370 to exit the at least one detent pocket 364. The applied force then moves the snorkel 366 relative to the carriage 356 and into the channel 322.

The snorkel 366 is configured to enter the channel 322 with the plunger plug 378 exiting the channel 322 upon finishing the expulsion of the contents from the barrel 310. As shown in FIGS. 7 and 8, the bulbous member 352 of the second end portion 350 of the pushrod 344 is configured to be releasably received within the catch 382 of the tip portion 354 to form an axial-tension limiting joint 386, similar in configuration and function to the axial-tension limiting joint 286 described above with respect to the second embodiment syringe 200. Because the major diameter 380 of the plunger plug 378 is greater than the channel diameter 324, movement of the plunger 340 in direction B results in the second end portion 350 of the pushrod 340 separating from the catch 382 in the tip portion 354 because the contact of the plunger plug 378 abutting the hub 330 inhibits movement of the tip portion 354.

FIG. 8 illustrates a fourth embodiment tip portion 400 with at least one fin 458 in which at least one slot 488 is provided in a plunger plug 478 of a snorkel 466 according to the present invention. The slot 488 is preferably configured to allow contents to flow past the plunger plug 478 when in use.

The foregoing is illustrative only of the principles of embodiments according to the present invention. Modifications and changes will readily occur to those skilled in the art, so it is not desired to limit the invention to the exact disclosure herein provided. While the preferred embodiment has been described, the details may be changed without departing from the invention, which is defined by the claims.

What is claimed is:

1. A syringe comprising:
   a barrel extending from an open proximal end to an open distal end, the barrel including a through-bore extending inward from the open proximal end and a channel extending inward from the open distal end, the through-bore and channel being in fluid communication, wherein the through-bore comprises a through-bore diameter and the channel comprises a channel diameter that is smaller than the through-bore diameter along a channel length;
   a plunger slidably received within the barrel through the open proximal end, the plunger comprising a pushrod coupled to a tip portion through a mating engagement; and
   a carriage disposed about and releasably engaged with the tip portion, wherein a force of engagement between the carriage and the tip portion maintains the carriage in a stationary position with respect to the tip portion as the pushrod is moved in a distal direction, and
   further wherein the carriage circumferentially physically contacts the barrel, and longitudinally contacts an end of the through-bore and additional pressure applied to the proximal end of the pushrod in the distal direction overcomes the force of engagement to allow the carriage to slide along the tip portion as the tip portion continues to move in the distal direction.

2. A syringe according to claim 1, further comprising a snorkel extending from and supported by the tip portion, the snorkel having a snorkel length that is greater than the channel length, the snorkel terminating in a free end including a plunger plug, the plunger plug having a major diameter that is greater than the channel diameter.

3. A syringe according to claim 1, wherein the mating engagement comprises a bulbous member received within a catch.

4. A syringe according to claim 3, wherein frictional forces between the carriage and the barrel in the distal direction are greater than a coupling force at the mating engagement, such that when the pushrod is moved in a proximal direction, the mating engagement will break before the tip portion is moved in the proximal direction.

* * * * *